United States Patent [19]

Hashimoto et al.

[11] Patent Number: 5,272,180

[45] Date of Patent: Dec. 21, 1993

[54] CELL PROLIFERATION INHIBITOR

[75] Inventors: Naoto Hashimoto; Kaneyoshi Kato, both of Suita; Yoshio Kozai, Toyonaka, all of Japan

[73] Assignee: Takeda Chemical Industries, Ltd., Osaka, Japan

[21] Appl. No.: 906,304

[22] Filed: May 8, 1992

Related U.S. Application Data

[60] Division of Ser. No. 754,209, Aug. 27, 1991, abandoned, which is a continuation of Ser. No. 579,086, Sep. 7, 1990, abandoned, which is a continuation of Ser. No. 235,575, Jul. 26, 1988, abandoned.

[30] Foreign Application Priority Data

Jul. 29, 1987 [JP] Japan .................. 62-189143

[51] Int. Cl.$^5$ .............................................. A61K 31/19
[52] U.S. Cl. .................................................... 514/575
[58] Field of Search ......................................... 514/575

[56] References Cited

FOREIGN PATENT DOCUMENTS 0171251 2/1986 European Pat. Off. ........ 260/396 R
0232089 8/1987 European Pat. Off. ........ 260/396 R Primary Examiner—Jerome D. Goldberg
Attorney, Agent, or Firm—Wenderoth, Lind & Ponack

[57] ABSTRACT

A compound of the formula:

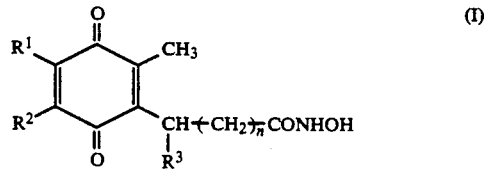

wherein, $R^1$ and $R^2$ are the same or different/representing methyl or methoxy groups, or form —CH=CH—CH=CH— by binding to each other; $R^3$ is an aromatic group or a heterocyclic group which may be substituted; and n is an integer of 2 to 8, shows inhibitory effect of cell proliferation and is useful as cell proliferation inhibitor.

3 Claims, No Drawings

CELL PROLIFERATION INHIBITOR

This is a divisional application of now abandoned Ser. No. 07/754,209 filed Aug. 27, 1991, which is a continuation of now abandoned Ser. No. 07/579,086 filed Sep. 7, 1990, which is a continuation of now abandoned Ser. No. 07/235,575 filed Jul. 26, 1988.

This invention relates to a cell proliferation inhibitor containing, as an effective ingredient, a hydroxamic acid derivative, which is effective in treatment of cancer and autoimmune diseases. More specifically, this invention relates to a hydroxamic acid derivative which is effective in inhibiting the proliferation of tumor cells in a mammal which cells are sensitive to treatment with the derivative, and the method therefor.

Cell proliferation is an essential function for growth of organisms and for maintenance of their lives. In higher animals, most, tissues and organs have their own proliferation mechanisms which are controlled by various regulating systems. Recently, many substances that control cell proliferation, i.e. "cell growth factors", have been isolated, purified, and clarified to play important roles in construction and maintenance of individual bodies. On the other hand, there are many reports that abnormal proliferation, especially out-of-control, unlimited proliferation may be involved in various diseases. Cancer is a representative example. It has been clarified that tumor cells release angiogenic substances to maintain their proliferation so that peripheral and inside regions of the cancer tissues are neovascularized; it has been almost clarified that the factors (angiogenic factors) are very effective for proliferation of vascular endothelial cells. Neovascularization is also observed in the pathological conditions such as chronic inflammation, diabetic retinopathy, psoriasis, rheumatic arthritis, etc., and has been suggested to be involved in progress of these diseases.

It has been also known that growth factors are involved in activation of immunocytes, particularly of lymphocytes, and therefore overproduction or overresponse to the growth factors may be some aggravating factors in autoimmune diseases and allergic diseases. Therefore, if a drug that can selectively inhibit the growth factors, involved in these diseases or suppress the response of the factors, could be developed, the drug would be an effective measure for treatment of these diseases and also for suppressing rejection in transplantation.

This invention provides a cell-prolifaration inhibitor and a hydroxamic acid derivative, having inhibitory activity of cell proliferation.

This invention relates to

1) A pharmaceutical composition for inhibiting cell proliferation in mammals, which contains an effective amount of a compound of the formula:

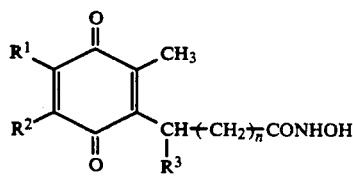

(I)

wherein, $R^1$ and $R^2$ are the same or different, representing methyl or methoxy groups, or form —CH═CH—CH═CH— by binding to each other; $R^3$ is an aromatic group or a heterocyclic group which may be substituted; and n is an integer of 2 to 8, and pharmaceutical acceptable carrier, vehicle or diluent therefor.

2) A compound of the formula:

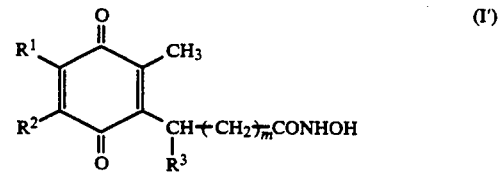

(I')

wherein $R^1$, $R^2$ and $R^3$ have the meanings given above and m is 5 or 6.

The cell-proliferation inhibitor is the pharmaceutical composition shown above.

The aromatic groups represented by $R^3$ in the general formula (I) described above include aryl groups such as phenyl, naphthyl, and indanyl (4-indanyl, 5-indanyl) groups, and the heterocyclic groups include 5- or 6-membered monocyclic or bicyclic groups containing at least one of oxygen, nitrogen, or sulfu- atoms as the ring-constituting atoms, such as thienyl (2-thienyl, 3-thienyl), furyl (2-furyl, 3-furyl), pyridyl (2-pyridyl, 3-pyridyl, 4-pyridyl), quinolyl (4-quinolyl, 8-quinolyl), and isoquinolyl (4-isoquinolyl, 8-isoquinolyl). Among these, phenyl and thienyl groups are desirable. These aromatic and heterocyclic groups may have one to five, desirably one to three, substituents at any positions, and the substituents include halogen atoms such as fluorine, chlorine, and bromine atoms, alkyl groups having one to three carbon atoms such as methyl, ethyl, and propyl groups, and alkoxy groups having one to three carbon atoms such as methoxy, ethoxy, and isopropoxy groups.

As the $R^3$, phenyl, 4-fluorophenyl, 4-methoxyphenyl, 5-methyl-2-thienyl are preferable. The symbol n is preferably an integer of 4 to 6 and the most preferably 5 or 6.

The compound of the formula (I) can be prepared by reacting a compound of the formula:

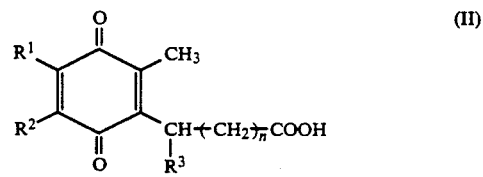

(II)

wherein each symbol has the meaning given above, with a carboxylic acid-activator to give a derivative which is reactive at the carboxylic group, followed by the reaction with hydroxylamine.

The carboxylic acid-activation include thionyl chloride, phosphorus pentachloride, chloroformic acid esters (methyl chloroformate, ethyl chloroformate), oxalyl chloride and carbodiimides (N,N-dicyclohexylcarbodiimide (DCC)), and a carbodiimdie and p-nitrophenol or hydroxysuccinimide may be combined. The reaction is carried out usually in the presence of a halogenated hydrocarbon such as methylene chloride and chloroform, an ether (such as tetrahydrofuran (THF), dioxane, dimethyl-ether, diethylether, and isopropylether), N,N-dimethylformamide, or a mixture thereof. The reaction temperature is usually −10° C. to 50° C.

When thionyl chloride, oxalyl chloride, or phosphoruspentachloride is used as the carboxylic acid-activator in the reaction, the reactive derivative obtained is an acid halide; when a chloroformic ester is used as the carboxylic acid-activator, the reactive derivative obtained is a mixed acid anhydride; and when a carbodiimide is used as the carboxylic acid-activator, the reactive derivative obtained is an active ester.

The reaction between the derivative which is reactive at the carboxyl group and hydroxylamine is carried out, when the reactive derivative is an acid halide, in a solvent such as dichloromethane, tetrahydrofuran, and acetone, in the presence of an acid-binding agent (pyridine, triethylamine, potassium carbonate, sodium carbonate, potassium hydrogencarbonate, sodium hydrogencarbonate, etc.) under anhydrous or hydrous conditions. The reaction temperature is about $-10°$ C. to about $30°$ C. When the reactive derivative is an active ester or a mixed acid anhydride, the reaction can be carried out in the same solvent as used in the reaction of the compound (II) with a carboxylic acid activator. The reaction temperature in this case is usually 0 to $30°$ C., and the reaction time is 1 to 5 hours.

The hydroxamic acid derivatives (I) thus produced can be isolated by the per se known methods of separation and purification (e.g. chromatography, crystallization).

The hydroxamic acid derivatives (I) have an asymetric carbon atom at the alpha (a) carbon on the side chain of the quinone nucleus of the structure. This means that the compounds (I) include optically active compounds and racemic compounds.

The compounds (I) can inhibit the proliferation of various cells (endothelial cells, lymphocytes, tumor cells, etc.), and therefore they can inhibit neovascularization, immunity, and proliferation of tumor cells. In addition, the compounds have extremely low toxicity, rarely giving rise to side effects. Therefore the compounds (I) are useful for treatment of the diseases such as diabetic retinopathy, psoriasis, rheumatism, chronic inflammation, autoimmune diseases, and cancer in mammals (mouse, rat, rabbit, monkey, horse, human, etc.). The compounds are also useful to suppress rejection in transplantation.

In addition the compounds (I) can improve the metabolism of poly-unsaturated fatty acids (linoleic acid, γ-linolenic acid, a-linolenic acid, arachidonic acid, dihomo-γ-linolenic acid, eicosapentaenoic acid), particularly they inhibit the production of oxygenated fatty acids (anti-oxidant activity) and metabolisms of the 5-lipoxygenase system (e.g. leukotrienes, 5-hydroxyeicosatetraenoic acid, 5-peroxyeicosatetraenoic acid, lipoxins, $LTB_4$, etc.); the compounds are expected to be effective in treatment of bronchial asthma, inflammation, immediate hypersensitivity, arteriosclerosis, atherosclerosis, fatty liver, hepatitis, cirrhosis of the liver, hypersensitivity pneumonia, etc.; the compounds are useful as drugs such as those for asthma, antiallergic agents, cerebrocardiovascular system-improving agents, coronary sclerosis-preventive-agents, immunoregulatory agents, prostaglandin-thromboxane metabolism-improving agents, therapeutics for fatty liver, hepatitis, cirrhosis of the liver, and hypersensitivity pneumonia, etc.

The cell-proliferation inhibitor of the present invention is a pharmaceutical composition containing a compound of the formula (I) and a pharmaceutically acceptable carrier, vehicle or diluent therefor. The pharmaceutical composition may be tablets, capsules (e.g. soft capsules, microcapsules), granules, powders, liquid preparations, injections, suppositories, etc. These pharmaceutical preparations can be prepared by a per se known conventional method.

Though the dose level varies according to the subjects, route of administration, symptoms, etc., for example, for oral or parenteral administration to an adult patient, the daily dose of compound (I) is about 0.1 mg/kg to 40 mg/kg body weight, desirably about 0.2 mg/kg to 20 mg/kg body weight.

Each of the compounds (I) has a bulky group at the alpha (a) carbon atom, and this characteristic structure makes it difficult to be inactivated in in vivo metabolism; therefore the effective blood level of the drug can be maintained for a longer period and the drug has an excellent effect at a lower dose, as compared with the known quinone compounds.

Among the compounds of the formula (I), the compounds of the formula (I') are novel compounds.

The compounds (II) can be prepared for example by the method described in the gazette of Japanese Unexamined Patent Publication No. 44840/1986.

Because the novel hydroxamic acid derivatives in this invention can inhibit cell proliferation, neovascularization, and proliferation of tumor cells, and suppress immunity, the derivatives can be used not only as anticancer agents but also for suppression of rejection in transplantation.

EXAMPLE 1

7-(4-Methoxyphenyl)-7-(3,5,6-trimethyl-1,4-benzoquinon-2-yl)-heptanoic acid (1.3 g, 3.3 mmol) was dissolved in dichloromethane (20 ml), to which oxalyl chloride (1 ml) was added at room temperature. The reaction mixture was stirred at $50°$ C. for 1 hour, and the solvent was evaporated under reduced pressure. The resultant residue was dissolved in THF (5 ml), which was added dropwise at room temperature to a mixture of hydroxylamine hydrochloride (1 g, 14 mmol) in THF (10 ml) and saturated solution of aqueous sodium hydrogencarbonate (10 ml). After being stirred at room temperature for 1 hour, ethyl acetate (20 ml) was added to the reaction mixture. The organic layer was washed with water, dried, and concentrated under reduced pressure, to give 7-(4-methoxyphenyl)-7-(3,5,6-trimethyl-1,4-benzoquinon-2-yl)-heptanohydroxamic acid (0.6 g, 42%). The physical properties are shown in the column of Compound No.8 in Table 1. In the similar manner, Compounds Nos. 1, 4, 10, 11, 12, 13, 14, 15, 16, 17, 19, 20, 21, 22, 23, 24, 25, and 26 were synthesized.

EXAMPLE 2

7-(4-Fluorophenyl)-7-(3,5,6-trimethyl-1,4-benzoquinon-2-yl)-heptanoic acid (0.8 g, 2.2 mmol) was dissolved in dichloromethane (20 ml), to which oxalyl chloride (0.5 ml) was added at room temperature. The reaction mixture was stirred at $50°$ C. for 1 hour, and the solvent was evaporated under reduced pressure The resultant residue was dissolved in THF (5 ml), which was added dropwise at room temperature to a mixture of hydroxylamine hydrochloride (0.5 g, 7 mmol) in THF (10 ml) and saturated solution of aqueous sodium hydrogencarbonate (10 ml). After being stirred at room temperature for 1 hour, ethyl acetate (20 ml) was added to the reaction mixture. The organic layer was washed with water, dried, and concentrated under reduced pressure, and the resultant residue was recrystallized from isopropylether, to give 7-(4-fluorophenyl)-7-(3,5,6-trimethyl-1,4-benzoquinon-2-yl)-heptanohydroxamic acid (0.7 g, 85%). The physical properties are shown in the column of Compound No.6 in Table 1. In the similar manner, Compounds Nos. 2, 3, 5, 7, 9, and 18 were synthesized.

TABLE 1

| Compound No. | $R^1$ | $R^2$ | $R^3$ | n | molecular formula boiling point (°C.) | NMR spectra (in CDCl$_3$), δ(ppm) |
|---|---|---|---|---|---|---|
| 1 | Me | Me | 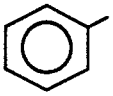 | 2 | $C_{19}H_{21}NO_4$ oil | 1.96(6H, s), 2.02(3H, s), 2.0-2.6(4H, m), 4.31(1H, t, 7Hz), 7.24(5H, m) |
| 2 | Me | Me | 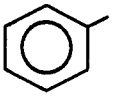 | 4 | $C_{21}H_{25}NO_4$ 59-60 | 1.1-1.8(4H, m), 2.0-2.4(4H, m), 1.97(6H, s), 2.03(3H, s), 4.26(1H, t, 7Hz), 7.27(5H, m) |
| 3 | Me | Me | 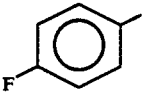 | 4 | $C_{21}H_{24}NO_4F$ 98-99 | 1.1-1.8(4H, m), 2.0-2.4(4H, m), 1.96(6H, s), 2.03(3H, s), 4.21(1H, t, 7Hz), 6.94(2H, m), 7.21(2H, m) |
| 4 | Me | Me | 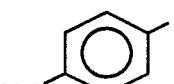 | 4 | $C_{22}H_{27}NO_5$ oil | 1.0-1.8(4H, m), 2.0-2.4(4H, m), 1.97(6H, s), 2.04(3H, s), 3.75(3H, s), 4.19(1H, t, 7Hz), 6.80(2H, d, 8Hz), 7.19(2H, d, 8Hz) |
| 5 | Me | Me | 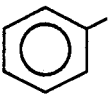 | 5 | $C_{22}H_{27}NO_4$ 60-61 | 1.1-1.8(4H, m), 2.0-2.4(4H, m), 1.97(6H, s), 2.02(3H, s), 4.27(1H, t, 7Hz), 7.22(5H, m) |
| 6 | Me | Me | 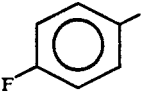 | 5 | $C_{22}H_{26}NO_4F$ 97-98 | 1.1-1.8(6H, m), 2.0-2.4(4H, m), 1.96(6H, s), 2.04(3H, s), 4.21(1H, t, 7Hz), 6.94(2H, m), 7.26(2H, m) |
| 7 | Me | Me | 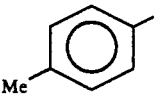 | 5 | $C_{23}H_{29}NO_4$ 69-70 | 1.1-1.8(6H, m), 2.0-2.4(4H, m), 1.96(6H, s), 2.02(3H, s), 2.27(3H, s), 4.21(1H, t, 7Hz), 7.09(4H, m) |
| 8 | Me | Me | 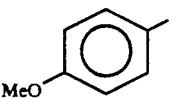 | 5 | $C_{23}H_{29}NO_5$ oil | 1.1-1.8(6H, m), 2.0-2.4(4H, m), 1.97(6H, s), 2.04(3H, s), 3.75(3H, s), 4.18(1H, t, 7Hz), 6.78(2H, d, 8Hz), 7.20(2H, d, 8Hz) |
| 9 | Me | Me | 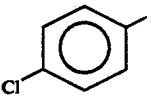 | 5 | $C_{22}H_{26}NO_4Cl$ 58-59 | 1.1-1.8(6H, m), 2.0-2.4(4H, m), 2.00(6H, s), 2.05(3H, s), 4.20(1H, t, 7Hz), 7.23(4H, m) |
| 10 | Me | Me | 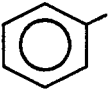 | 6 | $C_{23}H_{29}NO_4$ oil | 1.1-1.8(8H, m), 2.0-2.4(4H, m), 1.99(6H, s), 2.04(3H, s), 4.03(1H, t, 7Hz), 7.27(5H, m) |
| 11 | | | 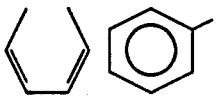 | 3 | $C_{22}H_{21}NO_4$ oil | 1.4-1.8(2H, m), 2.0-2.4(4H, m), 2.17(3H, s), 4.49(1H, t, 7Hz), 7.26(5H, m), 7.66(2H, m), 8.09(2H, m) |
| 12 | | |  | 4 | $C_{23}H_{23}NO_4$ oil | 1.1-1.8(4H, m), 2.0-2.4(4H, m), 4.49(1H, t, 7Hz), 7.23(5H, m), 7.70(2H, m), 8.03(2H, m) |

TABLE 1-continued

| Compound No. | R¹ | R² | R³ | n | molecular formula boiling point (°C.) | NMR spectra (in CDCl₃), δ(ppm) |
|---|---|---|---|---|---|---|
| 13 | | | (cyclohexenyl) (2-thienyl-Me) | 4 | $C_{21}H_{21}NO_4S$ oil | 1.1–1.8(4H, m), 2.0–2.4(4H, m), 2.20(3H, m), 4.62(1H, t, 7Hz), 6.88(2H, m), 7.10(1H, m), 7.66(2H, m), 8.03(2H, m) |
| 14 | | | (cyclohexenyl) (4-F-phenyl-Me) | 5 | $C_{24}H_{24}NO_4F$ oil | 1.1–1.8(6H, m), 2.0–2.4(4H, m), 2.17(3H, s), 4.37(1H, t, 7Hz), 6.95(2H, m), 7.27(2H, m), 7.65(2H, m), 7.99(2H, m) |
| 15 | | | (cyclohexenyl) (phenyl-Me) | 6 | $C_{25}H_{27}NO_4$ oil | 1.1–1.8(8H, m), 2.0–2.4(4H, m), 2.19(3H, s), 4.40(1H, t, 7Hz), 7.24(5H, m) |
| 16 | MeO | MeO | (phenyl-Me) | 5 | $C_{22}H_{27}NO_6$ oil | 1.1–1.8(6H, m), 2.0–2.4(4H, m), 2.01(3H, s), 3.95(6H, s), 4.27(1H, t, 7Hz), 7.23(5H, m) |
| 17 | MeO | MeO | (phenyl-Me) | 3 | $C_{20}H_{23}NO_6$ oil | 1.4–1.8(2H, m), 2.0–2.4(4H, m), 2.01(3H, s), 3.94(6H, s), 4.26(1H, t, 7Hz), 7.23(5H, m) |
| 18 | | | (cyclohexenyl) (4-MeO-phenyl-Me) | 4 | $C_{22}H_{27}NO_5$ 115–116 | 1.1–1.8(4H, m), 2.0–2.4(4H, m), 2.19(3H, s), 3.74(3H, s), 4.36(1H, t, 7Hz), 6.80(2H, d, 8Hz), 7.28(2H, d, 8Hz), 7.64(2H, m), 8.01(2H, m) |
| 19 | | | (cyclohexenyl) (3,4-diMe-phenyl-Me) | 5 | $C_{26}H_{29}NO_4$ oil | 1.1–1.8(6H, m), 1.9–2.5(4H, m), 2.19(3H, s), 4.37(1H, t, 7Hz), 7.03(3H, m), 7.64(2H, m), 8.01(2H, m) |
| 20 | Me | Me | (3,5-diMe-phenyl-Me) | 5 | $C_{23}H_{29}NO_4$ oil | 1.1–1.8(6H, m), 1.9–2.4(4H, m), 1.98(6H, s), 2.03(3H, s), 4.23(1H, t, 7Hz), 7.05(4H, m) |
| 21 | Me | Me | (indanyl-Me) | 6 | $C_{26}H_{33}NO_4$ oil | 1.1–1.8(10H, m), 1.9–2.4(4H, m), 1.98(6H, s), 2.03(3H, s), 4.23(1H, t, 7Hz), 7.05(4H, m) |
| 22 | Me | Me | (3,4-diMe-phenyl-Me) | 5 | $C_{24}H_{31}NO_4$ oil | 1.1–1.8(6H, m), 1.9–2.5(4H, m), 1.96(6H, s), 2.03(3H, s), 2.19(6H, s), 4.20(1H, t, 8Hz), 6.98(3H, m) |
| 23 | | | (cyclohexenyl) (3,4-diMe-phenyl-Me) | 5 | $C_{26}H_{29}NO_6$ oil | 1.1–1.8(4H, m), 1.9–2.4(4H, mm), 2.20(3H, s), 3.84(6H, s), 4.37(1H, t, 7Hz), 6.83(3H, m), 7.66(2H, m), 8.02(2H, m) |
| 24 | | | (cyclohexenyl) (2,5-diMe-thienyl) | 5 | $C_{23}H_{24}NO_4S$ oil | 1.1–1.8(4H, m), 1.9–2.4(4H, m), 2.21(3H, s), 2.37(3H, s), 4.52(1H, t, 7Hz), 6.52(1H, d, 3Hz), 6.67(1H, d, 3Hz), 7.67(2H, m), 8.05(2H, m) |

TABLE 1-continued

| Compound No. | R¹ | R² | R³ | n | molecular formula boiling point (°C.) | NMR spectra (in CDCl₃), δ(ppm) |
|---|---|---|---|---|---|---|
| 25 | Me | Me | (naphthyl) | 5 | $C_{26}H_{29}NO_4$ oil | 1.1–1.8(6H, m), 1.81(3H, s), 2.0–2.4(4H, m), 1.97(3H, s), 2.03(3H, s), 5.05(1H, t, 7Hz), 7.2–7.8(7H, m) |
| 26 | Me | Me | (indanyl) | 5 | $C_{25}H_{31}NO_4$ oil | 1.1–1.8(8H, m), 2.96(6H, s), 2.01(3H, s), 2.83(4H, m), 4.21(1H, t, 7Hz), 7.15(3H, m) |

EXAMPLE 3

Preparation Example

| A) Capsules | |
|---|---|
| (1) Compound No. 5 | 50 mg |
| (2) very finely powdered cellulose | 30 mg |
| (3) lactose | 37 mg |
| (4) magnesium stearate | 3 mg |
| total | 120 mg |

Ingredients (1), (2), (3), and (4) were mixed and filled in gelatin capsules.

| B) Soft capsules | |
|---|---|
| (1) Compound No. 13 | 50 mg |
| (2) corn oil | 100 mg |
| total | 150 mg |

| C) Tablets | |
|---|---|
| (1) Compound No. 6 | 50 mg |
| (2) lactose | 34 mg |
| (3) corn starch | 10.6 mg |
| (4) corn starch (paste) | 5 mg |
| (5) magnesium stearate | 0.4 mg |
| (6) calcum carboxymethylcellulose | 20 mg |
| total | 120 mg |

According to the routine method these ingredients were mixed and compressed by a tableting machine.

Experiment 1 [Inhibition ($10^{-5}$ M) of 5-lipoxygenase from guinea pig polymorphonuclear leukocytes]

5-Lipoxygenase used was the enzyme preparation prepared from guinea pig peritoneal macrophage. For determination of the activity of lypoxygenase 25 μM [1-$^{14}$C]arachidonic acid ($5 \times 10^4$ cpm) as the substrate, 50 mM phosphate buffer solution (pH 7.4), 2 mM CaCl₂, 2 mM ATP, and a reaction mixture containing the enzyme (200 μl) were used. After preincubation at 25° C. for 2 minutes, [1-$^{14}$C]arachidonic acid ($5 \times 10^4$ cpm) was added, and allowed to react at 25° C. for 3 minutes; the resultant mixture was made acidic, and arachidonic acid and its metabolites were extracted with ether. Radioactivity of the ether layer was determined by silica gel thin layer chromatography using a mixture of petroleum ether:ethylether:acetic acid (15:85:0.1) as the eluant and the elution was performed at −10° C. After elution, the thin layer plate was subjected to autoradiography, the radioactive fractions were scraped out, and the radioactivity of the product was determined by counting. The agent was added two minutes before the beginning of the reaction.

| Compound No. | Inhibitory activity (%) |
|---|---|
| 5 | 74.6 |
| 6 | 79.3 |
| 8 | 83.8 |
| 14 | 89.7 |

Experiment 2 (Inhibition of the binding of U-46619 to platelet membrane fraction)

Blood sampling from guinea pigs and preparation of platelet membrane fraction were performed according to the method of S.C. Hung et al. [Biochim. Biophys. Acta, 728, 171–178 (1983)]. Blood was drawn from the heart of a Hartley strain guinea pig anesthetized with ether, and suspended in 3.15% sodium citrate solution (containing aspirin of the final concentration of 1 mM) (sodium citrate solution: whole blood=1:9). The blood treated with sodium citrate was centrifuged at 3000 rpm for 5 to 6 seconds, so that platelet rich plasma (PRP) was separated. The PRP was again centrifuged at 4° C. at 4800 rpm for 10 minutes, to give platelet pellet. The platelet pellet was washed with 30 ml of 25 mM Tris-HCl buffer (containing 5 mM, MgCl₂, pH 7.4), and suspended in the same buffer. After platelets were broken by a sonicator, the suspension was centrifuged at 10000 rpm for 1 hour, and the membrane fraction was suspended in the buffer. Determination of protein content was performed by using Biorad protein assay kit, and a suspension containing protein of 1–1.5 mg/ml was prepared.

Binding assay was performed as follows: A reaction mixture composed of 4 nM [$^3$H]U-46619, $10^{-5}$ M drug solution, and platelet membrane fraction containing 100 μg of protein was incubated at 25° C. (room temperature) for 30 minutes. The reaction mixture was filtrated through a glass filter (GF/C), and washed twice with the buffer described above; the glass filter was placed in 4 ml of liquid scintillator (anionic) for measurement of the radioactivity.

| Compound No. | IC₅₀ (M) |
|---|---|
| 8 | 6.0 |
| 14 | 2.6 |

Experiment 3 [Evaluation of inhibition of proliferation of human umbilical venous endothelial cells]

The human vascular endothelial cells were obtained by subculture of the cells, which had been obtained from human umbilical vein by perfusion with tripsin solution, in the culture medium which had been prepared by addition of 2.5% bovine fetal serum and 2.0 ng/ml of human recombinant fibroblast growth factor (abbreviated as rFGF hereinafter; prepared in Biotechnology Institute of our company) to GIT medium (Daigo Eiyou Kagaku).

One hundred μl of the suspension of $2 \times 10^3$ human vascular endothelial cells was inoculated to a 96-well culture plate (Nunc, 1-67008) and incubated in a gas-controlled thermostat. On the next day rFGF and 100 μl of a medium containing different concentrations of the test substance were added, so that the final concentration of rFGF might be 2 ng/ml. The test substance was dissolved in dimethylsulfoxide (DMSO hereinafter) solution, and the resultant solution was diluted so that the final DMSO concentration was 0.25% or less. After 3 days of incubation, the culture medium containing the test substance was aspirated off, 100 μl of 1 mg/ml MTT sol (3-(4,5-dimethyl-2-thiazolyl)-2,5-diphenyl-2H-tetrazolium bromide dissolved in the culture medium) was added, and the mixture was kept warm for 4 hours. Then 100 μl of 10% SDS solution (aqueous solution of sodium dodecylsulfate) was added and kept warm for 5-6 hours, so that the cells and MTT pigment were solubilized, and the $OD_{590}$ value was determined by spectrophotometer. The OD value of the control sample containing no test substance was taken as 100%, and the endothelial cell growth-inhibitory activity of the test substance was compared on the basis of the $IC_{50}$ value, the concentration of a compound at which 50% OD value is observed.

| Compound No. | $IC_{50}$ (μg/ml) |
|---|---|
| 1 | 10 |
| 2 | 0.63 |
| 3 | 1.25 |
| 4 | 0.63 |
| 5 | 0.63 |
| 6 | 1.25 |
| 7 | 1.25 |
| 8 | 0.63 |
| 9 | 1.25 |
| 10 | 25 |
| 11 | 5.0 |
| 12 | 0.08 |
| 13 | <0.08 |
| 14 | <0.63 |
| 15 | <0.63 |
| 16 | 1.25 |
| 17 | 20 |

Experiment 4 [Evaluation of inhibition of growth of IL-2-dependent cells (NKC-3)]

To each well of a 96-well microplate, 50 μl of NKC-3 cells ($4 \times 10^5$ cells/well), 20 μl of IL-2 solution (0.067 U/ml), and 40 μl of the test substance (DMSO solution) were added, which was incubated at 37° C. for 20 hours (culture medium: RPMI1640-20%ECS). To each well 20 μl of MTT solution was added, which was kept at 37° C. for 4 hours. Then 100 μl of 10% SDS solution was added to each well, which was kept still at 37° C. overnight so that the cells and MTT pigment were solubilized, and the absorbance at 590 nm was measured by spectrophotometer. The absorbance without test substance was taken as 100, and the concentration of a compound that showed 50% absorbance was the $IC_{50}$ value.

| Compound No. | $IC_{50}$ (M) |
|---|---|
| 5 | $4.1 \times 10^{-5}$ |

Experiment 5 [Assay of neo vascularization-inhibiting activity using chicken embryonal chorioallantois]

The procedure of the assay of neo vascularization-inhibiting activity using cultured chicken embryonal chorioallantois was a modification of the method of Taylor et al [S. Taylor & J. Folkman, Nature, 297, 307 (1982)]. Three-day-old fertilized eggs from which the shell had been removed were incubated, and 10 (or 11)-day-old embryos were used. An aqueous solution or an aqueous suspension of the test substance (100 μg) was dried on a transparent plastic disc together with ECGS (endothelial cell growth supplement, Collaborative Research Co.), a vascularizing agent, which was placed on the chorioallantois, and neo vascularization was evaluated after 2 (or 3) days under the stereoscopic microscope by comparing with a control specimen.

| Compound No. | Effectiveness |
|---|---|
| 8 | + |
| 9 | + |
| 14 | + |
| 15 | + |

Experiment 6

Five male ICR mice (8-week-old) in each group were used, and given subcutaneously 100 mg/kg/day of the test substance (Compound No.5) for 3 days. The solution for administration was prepared by dissolving the test substance in physiological saline containing 0.5% gum arabic, and given at the dose of 100 mg/10 ml/kg body weight.

Results

During the 4 days of observation after the start of the treatment with the test substance neither death occurred nor abnormality such as loss of body weight was observed.

We claim:

1. A method for inhibiting the proliferation of tumor cells in a mammal which cells are sensitive to treatment with the compound recited below, which comprises administering to a mammal an effective tumor cell proliferation inhibiting amount of a compound of the formula:

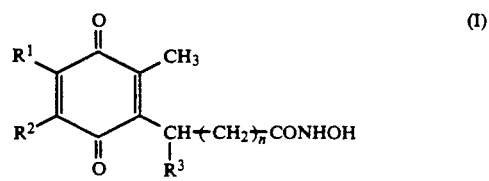

wherein, $R^1$ and $R^2$ are the same or different, representing methyl or methoxy groups, or form —CH=

CH—CH=CH— by binding to each other; R³ is phenyl or naphthyl, each of which may be independently substituted with a halogen, an alkyl having 1 to 3 carbon atoms, or an alkoxy having 1 to 3 carbon atoms; and n is an integer of 2 to 8; in a pharmaceutically acceptable carrier.

2. A method as claimed in claim 1, wherein n in the formula (I) is an integer of 4 to 6.

3. A method as claimed in claim 1, wherein R³ in the formula (I) is a phenyl group which may be substituted with fluorine or a methoxy.

* * * * *